United States Patent [19]

Maeda et al.

[11] Patent Number: 4,628,050

[45] Date of Patent: Dec. 9, 1986

[54] ANTINEPHRITIC PHARMACEUTICAL COMPOSITION CONTAINING 24, 25-DIHYDROXYCHOLECALCIFEROL AS AN ACTIVE INGREDIENT

[75] Inventors: Yuji Maeda, Nagareyama; Hideyuki Yamato; Takayoshi Fujii, both of Tokyo; Yasuhiko Kobayashi, Niiza; Kenichi Saito; Tadaaki Kato, both of Tokyo; Chikao Yoshikumi, Kunitachi, all of Japan

[73] Assignee: Kureha Kagaku Kogyo Kabushiki Kaisha, Tokyo, Japan

[21] Appl. No.: 800,114

[22] Filed: Nov. 20, 1985

[30] Foreign Application Priority Data

Nov. 27, 1984 [JP] Japan ................................ 59-250313

[51] Int. Cl.$^4$ .............................................. A61K 31/59
[52] U.S. Cl. ................................................... 514/167
[58] Field of Search ....................................... 514/167

[56] References Cited

U.S. PATENT DOCUMENTS 4,501,738  2/1985  Yamato et al. ..................... 514/167

Primary Examiner—Elbert L. Roberts
Attorney, Agent, or Firm—Cushman, Darby & Cushman

[57] ABSTRACT

Disclosed herein is a pharmaceutical composition in dosage unit form, which comprises a dosage effective for treating nephritic disease of a compound of 24,25-dihydroxycholecalciferol as an active ingredient and a pharmaceutically acceptable carrier.

4 Claims, No Drawings

ANTINEPHRITIC PHARMACEUTICAL COMPOSITION CONTAINING 24, 25-DIHYDROXYCHOLECALCIFEROL AS AN ACTIVE INGREDIENT

BACKGROUND OF THE INVENTION

The present invention relates to a pharmaceutical composition for treating nephritic disease, which contains 24,25-dihydroxycholecalciferol as an active ingredient, and more in detail, to a pharmaceutical composition for treating uremic disease which contains 24,25-dihydroxycholecalciferol as an active ingredient.

In the cases of chronic renal failure, the pertinent treatment is carried out according to each stage of the disease. Namely, in the compensatory stage, (1) dietetics and (2) conservative treatment mainly comprising the pharmaceutical treatments for improving the abnormally morbid state accompanying chronic renal failure are mainly carried out, and in the noncompensatory stage (the uremic stage) where the abnormally morbid state cannot be improved by the above-mentioned conservative treatment, methods for cleaning the blood of the patient mainly comprising the dialytic treatment and renal transplantation are the nucleus of the treatment of chronic renal failure.

Although the remarkable development of dialytic treatment in recent years has improved the results of the dialytic treatment, many of the patients suffering from the chronic renal failure have a strong desire of avoiding the dialytic treatment if possible or of postponing the starting of the dialytic treatment as far as possible. In order to meet the strong desire of the patients, the development of a new treatment of the chronic renal failure has been demanded. Such a development of a new treatment meets the social requirement for suppressing the increase of the treatment cost for carrying out the dialysis with the recent increase of the number of patients treated by dialysis.

As a result of the present inventors' study on the endogenous substances which exist in the healthy human body and of which the safety to human being has been verified, it has been found by the present inventors that 24,25-dihydroxycholecalciferol (hereinafter referred to as the present substance or 24,25-$(OH)_2$-$D_3$) has an antinephritic activity, and based on the above-mentioned finding, the present invention has been attained.

SUMMARY OF THE INVENTION

In a first aspect of the present invention, there is provided a pharmaceutical composition in dosage unit form, which comprises a dosage effective for the treatment of nephritic disease of a compound of 24,25-dihydroxycholecalciferol and a pharmaceutically acceptable carrier.

In a second aspect of the present invention, there is provided a method for treating nephritic disease, which comprises administering to a patient suffering from nephritic disease an effective amount of a compound of 24,25-dihydroxycholecalciferol.

DETAILED DESCRIPTION OF THE INVENTION

The present substance represented by the formula:

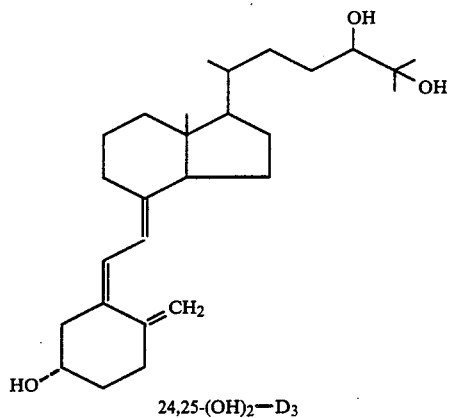

24,25-$(OH)_2$—$D_3$ includes the following two known compounds, 24R,25-dihydroxycholecalciferol and 24S,25-dihydroxycholecalciferol (hereinafter referred to as 24R,25-$(OH)_2$-$D_3$ and 24S,25-$(OH_2$-$D_3$, respectively), disclosed, for instance, in "Pharmacia", 10, 319–322.

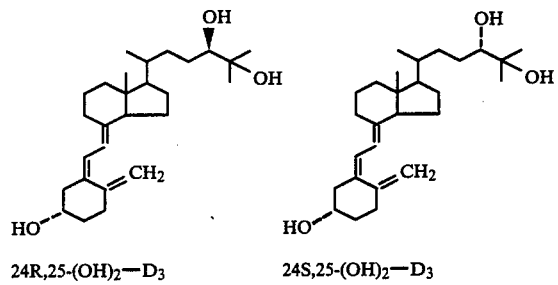

24R,25-$(OH)_2$—$D_3$    24S,25-$(OH)_2$—$D_3$

Namely, the present substance may be either of the above-mentioned two compounds, and further, may be any mixture thereof, however, more preferable compound is 24R,25-$(OH)_2$-$D_3$.

The pharmaceutical composition according to the present invention, which contains the present substance as an active ingredient, is used in the various forms as the pharmaceutical preparation as follows. The pharmaceutical composition for use in treating the nephritic disease may be orally, parenterally or rectally administered, however, it is preferably administered orally.

As the formulation of the pharmaceutical composition containing the present substance as an active ingredient, tablet, powder, granule, suppository, capsule, ethanolic solution, solution in oil, aqueous suspension, etc. may be mentioned for administration. As the oily solvent, triglyceride of a middle fatty acid, corn oil, cotton seed oil, peanut oil, fish liver oil, oily ester, etc. may be exemplified, and cacao oil and glycerol may be preferable as the solvent. As other component(s) of the pharmaceutical composition, lactose, starch, talc, magnesium stearate, sorbic acid, salt of sorbic acid, saccharide or derivative thereof, ethanol, aqueous physiological saline solution, surfactant, antioxidant, etc. may be used in combination with the present substance.

The content of the present substance in the pharmaceutical composition according to the present invention is from 0.00002 to 4% by weight, preferably from 0.0002 to 1% by weight.

The present substance is administered to an adult in an amount of from 0.1 to 100,000 μg per day, preferably from 0.5 to 10,000 μg per day.

The following is the result of examination of the acute mammalian toxicity of the present substance.

Acute mammalian toxicity of the present substance

An ethanolic solution of the present substance (24R,25 (OH)$_2$-D$_3$) was prepared, and the thus obtained solution was dissolved in triglyceride of a middle fatty acid (C$_8$ to C$_{10}$ fatty acid) so that the concentration of ethanol in the thus obtained solution is 2% by weight. The thus obtained solution was forcibly administered orally to each of 10 male ICR mice (body weight of 25±3 g) at a dose rate of 100 mg of the present substance/kg. As a result of observing the intoxication symptoms on the thus treated rats for 2 weeks, all the mice (10 animals) survived without any abnormality. After sacrificing all the mice, general blood examination biochemical blood examination, autopsy and histopathological examination were carried out on the blood specimen and the body of the mice.

The findings in the above-mentioned examinations were quite the same as those of the examinations carried out on the control mice to which only the triglyceride of a middle fatty acid was administered.

Accordingly, the present substance is an extremely safe substance as compared to 1α-(OH)-D$_3$ which is an active-type Vitamin D$_3$ with LD$_{50}$(p.o.) of less than 1 mg/kg because LD$_{50}$(p.o.) of the present substance is larger than 100 mg/kg and the administration of the present substance at a rate of 100 mg/kg caused no abnormal symptoms on the mice.

As a result of p.o. administering 24R,25-(OH$_2$-D$_3$ to each of the rats, from which the kidneys had been extirpated at a rate of 5/6, every day for 3 months continuously at a daily rate of 10 μg/kg the excreted amount of creatinine in the urine thereof was larger than that in the urine of the control rats. Namely, the present substance was effective in treating uremia.

The present substance is effective in treating uremia, various renal failures, nephritis, etc.

The present invention and the effectiveness of the present substance will be explained more in detail while referring to the non-limitative examples as follows.

EXAMPLE 1

Preparation of the capsule of the present substance

Triglyceride of a middle fatty acid (C$_8$ to C$_{10}$ fatty acid) was irradiated by ultraviolet rays from a high-pressure mercury lamp of 400 W under argon-bubbling for 72 hours, thereby eliminating peroxide contained in the triglyceride, and into 1 kg of the thus treated triglyceride (hereinafter referred to as MCT), 5 mg of 24R,25-(OH$_2$-D$_3$ were dissolved. By using the thus prepared solution and a molten mixture of the following components of the wall-membrane of the capsules (prepared by heating the components) in a soft capsule forming machine, capsules each containing 0.5 μg, 1.0 μg, 2.0 μg, 5.0 μg or 10.0 μg of 24R,25-(OH)$_2$-D$_3$ were prepared.

Components of the wall-membrane of the capsule 10 parts by weight of gelatin
2 parts by weight of glycerol
0.05 part by weight of an antiseptic agent (ethylparaben produced by Mallinckrodt Inc.)
0.2 part by weight of titan white
0.2 part by weight of water (part by weight in the final form of capsules)

EXAMPLE 2

Subacute mammalian toxicity test

A solution of 24R,25-(OH,$_2$-D$_3$ dissolved in a solvent (Panasate ® 810 produced by Nippon Oil Fats Co., Ltd.) containing 1% by weight of ethanol was forcibly administered orally to each of 10 male and female ICR mice daily and continuously for 30 days at the respective daily dose rates of 10, 100 and 1000 μg/kg, and the body weight of all the mice was recorded every day of administration to prepare the growth curve. After finishing the 30 day-administration, all the mice were sacrificed and subjected to autopsy while taking the blood specimen therefrom. The same procedures were carried out on the control group to which only the solvent was administered in the same schedule as above.

According to the growth curve (body weight vs. day) of the thus treated mice, no significant difference of body weight change was observed among all the groups including the control group.

As a result of histopathological examination of the following extirpated organs of all the mice after fixing the organs with an aqueous 10% solution of formaldehyde and staining thereof with hematoxylin and eosin, no abnormal finding was obtained on all the organs as follows.

Brain, heart, lung, liver, kidney, adrenal, spleen, pancreas, thyroid, pituitary, thymus, mesenteric lymph node, testis, ovary, uterus, stomach, small intestine (jejunum, ileum and duodenum), large intestine (colon and caecum), eye-ball, submaxillary gland, bladder, skin of the back, muscle, sternum, sternal marrow, femur and femural marrow.

TABLE 1:

Test result of general examination of blood

| Group | Sex | Dose rate (μg/kg) | Number of Erythrocyte | Leukocyte | Hemoglobin | Hematocrit value |
|---|---|---|---|---|---|---|
| 1 | male | 10 | none[1] | none | none | none |
| 2 | male | 100 | none | none | none | none |
| 3 | male | 1000 | none | none | none | none |
| 4 | female | 10 | none | none | none | none |
| 5 | female | 100 | none | none | none | none |
| 6 | female | 1000 | none | none | none | none |

Note:
[1]none: means that no difference was found between the group administered with the present substance and the group subjected to false operation and administered only with the solvent.

TABLE 2:

Test results of blood biochemical examination

| Group | Sex | Dose rate (μg/kg) | GOT | GPT | LDH | Ca | I-P | ALP | T-P | A/G | Alb | T-Bil | Glu | T-CHO | BUN |
|---|---|---|---|---|---|---|---|---|---|---|---|---|---|---|---|
| 1 | male | 10 | n[1] | n | n | n | n | n | n | n | n | n | n | n | n |
| 2 | male | 100 | n | n | n | n | n | n | n | n | n | n | n | n | n |

TABLE 2:-continued

| | | Dose rate | Test results of blood biochemical examination Item | | | | | | | | | | | | |
|---|---|---|---|---|---|---|---|---|---|---|---|---|---|---|---|
| Group | Sex | (μg/kg) | GOT | GPT | LDH | Ca | I-P | ALP | T-P | A/G | Alb | T-Bil | Glu | T-CHO | BUN |
| 3 | male | 1000 | n | n | r[2] | n | n | n | n | n | n | r | r | n | r |
| 4 | female | 10 | n | n | n | n | n | n | n | n | n | n | n | n | n |
| 5 | female | 100 | n | n | n | n | n | n | n | n | n | n | n | n | n |
| 6 | female | 1000 | n | n | n | n | n | n | n | n | n | n | n | n | n |

Notes:
[1]"n" means that no difference was observed between the group administered with the present substance and the group subjected to false operation and administered only with MCT.
[2]"r" means that the level of the group administered with the present substance is lower than that of the group subjected to false operation and administered only with MCT.

TABLE 3:

| | | | Test results of urinalysis | | | | | |
|---|---|---|---|---|---|---|---|---|
| | | Dose rate | | Item | | | | |
| Group | Sex | (μg/kg) | pH | sugar | protein | Occult blood | Ketone body | urobilinogen |
| 1 | male | 10 | n[1] | n | n | n | n | n |
| 2 | male | 100 | n | n | n | n | n | n |
| 3 | male | 1000 | n | n | n | n | n | n |
| 4 | female | 10 | n | n | n | n | n | n |
| 5 | female | 100 | n | n | n | n | n | n |
| 6 | female | 1000 | n | n | n | n | n | n |

Note:
[1]"n" means that no difference was observed between the group administered with the present substance and the group subjected to false operation and administered only with MCT.

TABLE 4:

| | | | Weight of internal organs | | | | | | | | | | |
|---|---|---|---|---|---|---|---|---|---|---|---|---|---|
| | | Dose rate | Organ[1] | | | | | | | | | | |
| Group | Sex | (μg/kg) | B | P | H | L | Li | S | K | Ad | Th | T | O | U |
| 1 | male | 10 | n[2] | n | n | n | n | n | n | n | n | n | | |
| 2 | male | 100 | n | n | n | n | n | n | n | n | n | n | | |
| 3 | male | 1000 | n | n | n | n | n | n | n | n | n | n | | |
| 4 | female | 10 | n | n | n | n | n | n | n | n | n | | n | n |
| 5 | female | 100 | n | n | n | n | n | n | n | n | n | | n | n |
| 6 | female | 1000 | n | n | n | n | n | n | n | n | n | | n | n |

Notes:
[1]Name of organs: B: brain, P: pituitary, H: heart, L: lung, Li: liver, S: spleen, K: kidneys, Ad: adrenal, Th: thymus, T: testes, O: ovaries and U: uterus
[2]"n" means the same as in the table 3.

EXAMPLE 3

Test on antiuremic activity of the present substance 16 male Wistar rats after 7 weeks of birth were subjected to extirpation of the kidneys thereof to the extent of 5/6 while following the method of Ogura (refer to Journal of Japan Nephrological Society, Vol. 22, pp 825-831, 1980), and after dividing the thus treated rats into two groups, a solution of 24R,25-(OH,$_2$-D$_3$ in an aqueous 0.02% solution of isopropyl alcohol was forcibly administered p.o. once a day continuously for 3 months from the third day of operation at a daily dose rate of 10 μg of 24R,25-(OH,$_2$-D$_3$/kg to each rat of the first group, each rat of the second group being administered only with the same amount of the aqueous 0.02% solution of isopropyl alcohol in the same manner as in the first group.

After breeding the two groups of the thus treated rats for 3 months, each rats was transferred to each of the metabolic-cages to collect the whole amount of urine excreted in 24 hours.

The amount of the thus collected urine and the amount of the excreted creatinine in the urine were measured the results being shown as follows

| Group No. | Amount of urine (ml/24 hours) | Amount of creatinine excreted in the urine (mg/24 hours) |
|---|---|---|
| 1 | 35.6 ± 8.9 | 14.0 ± 7.5*[1] |
| 2*[2] | 38.4 ± 8.9 | 5.73 ± 5.9 |

Notes:
*[1]$p < 0.05$
*[2]Control group (administered only with the solvent)

As are seen in the above-mentioned data, each rat of the first group administered with 24R,25-(OH,$_2$-D$_3$ excreted a significantly larger amount of creatinine in the urine thereof as compared to each rat of the control group. As has been well known, the amount of excreted creatinine detected in urine in 24 hours is used to know the body state, particularly concerning uremia. Namely 24R,25-(OH,$_2$D$_3$ has an antiuremic activity.

What is claimed is: pg,17

1. A method for the treatment of uremia, renal failure and nephritis, which comprises administering to a patient suffering from uremia, renal failure or nephritis a therapeutically effective amount of a compound of 24,25-dihydroxycholecalciferol.

2. A method according to claim 1, wherein the compound is 24R,25-dihydroxycholecalciferol.

3. A method for the treatment of uremia, which comprises administering to a patient suffering from uremia a therapeutically effective amount of a compound of 24,25-dihydroxycholecalciferol.

4. A method according to claim 3, wherein the compound is 24R,25-dihydroxycholecalciferol.

* * * * *